United States Patent [19]

Su et al.

[11] Patent Number: 5,383,942
[45] Date of Patent: * Jan. 24, 1995

[54] FUEL COMPOSITION

[75] Inventors: Wei-Yang Su, Austin, Tex.; Sheldon Herbstman, New City; Joseph M. Russo, Poughkeepsie, both of N.Y.; Robert L. Zimmerman; Michael Cuscurida, both of Austin, Tex.

[73] Assignee: Texaco Inc., White Plains, N.Y.

[*] Notice: The portion of the term of this patent subsequent to Apr. 20, 2010 has been disclaimed.

[21] Appl. No.: 79,571

[22] Filed: Jun. 22, 1993

[51] Int. Cl.$^6$ ............................................. C10L 1/10
[52] U.S. Cl. ...................................... 44/334; 44/418; 564/196
[58] Field of Search .................... 44/330, 419, 418; 564/193, 194, 196

[56] References Cited

U.S. PATENT DOCUMENTS

| | | | |
|---|---|---|---|
| 4,234,321 | 11/1980 | Lilburn | 44/72 |
| 4,357,148 | 11/1982 | Graiff | 44/62 |
| 4,581,040 | 4/1986 | Sung et al. | 44/71 |
| 4,604,103 | 8/1986 | Cambell | 44/72 |
| 4,631,069 | 12/1986 | Sung | 44/56 |
| 4,643,738 | 2/1987 | Sung et al. | 44/63 |
| 4,659,337 | 4/1987 | Sung | 44/63 |
| 4,787,851 | 5/1988 | Sung et al. | 44/72 |
| 5,203,879 | 4/1993 | Su et al. | 44/419 |
| 5,234,478 | 8/1993 | Su et al. | 44/418 |

*Primary Examiner*—John Niebling
*Assistant Examiner*—Edna Wong
*Attorney, Agent, or Firm*—Jeffrey M. Greenman

[57] ABSTRACT

An amido alkanolamine composition obtained by reacting, at a temperature of 10° C.–200° C.:

(a) a 4-alkyl-2-morpholinone represented by the formula:

$$R-N\underset{\diagdown\phantom{X}\diagup}{\overset{\diagup\phantom{X}\diagdown}{\phantom{XX}}}O\overset{\displaystyle O}{\underset{\phantom{X}}{\parallel}}$$

in which R represents a monovalent aliphatic radical having from 1 to 10 carbon atoms; and (b) a hydrocarbyl oxypolyoxyalkylene amine represented by the formula $$R'-O\left[CH_2-\underset{R'''}{CH}-O\right]_x CH_2-\underset{R'''}{CH}-NH_2$$

in which R' represents an alkyl, an alicyclic or an alkylalicyclic radical having from 12 to 30 carbon atoms or $$R''-\text{(phenyl)}$$

wherein R'' represents a hydrocarbyl radical having from 4 to 30 carbon atoms, x has a value of from about 5 to 50, and R''' is an ethyl radical or a mixture of methyl and ethyl radicals.

12 Claims, No Drawings

FUEL COMPOSITION

BACKGROUND OF THE INVENTION

1. Field of the Invention

This invention relates to a novel additive composition for use in motor fuels. The additive comprises the reaction product obtained by reacting a 4-alkyl-2-morpholinone with a hydrocarbyl oxypolyoxyalkylene amine to produce a motor fuel—soluble amidoalkanolamine compound which provides a number of valuable properties in a motor fuel composition.

The combustion of a hydrocarbon motor fuel in an internal combustion engine leads to the formation and accumulation of deposits on various parts of the combustion chamber as well as on the fuel intake and exhaust system of the engine. The presence of deposits in the combustion chamber seriously reduces the operating efficiency of the engine. First, deposit accumulation within the combustion chamber inhibits heat transfer between the chamber and the engine cooling system. This leads to higher temperatures within the combustion chamber, resulting in increases in the end gas temperature of the incoming charge. Consequently, end gas auto-ignition occurs causing engine knock. In addition, the accumulation of deposits within the combustion chamber reduces the volume of the combustion zone, causing a higher than design compression ratio in the engine. This, in turn, can also lead to engine knocking. A knocking engine does not effectively utilize the energy of combustion. Moreover, a prolonged period of engine knocking can cause stress fatigue and wear in pistons, connecting rods, bearings and cam rods of the engine. The phenomenon noted is characteristic of gasoline powered internal combustion engines. It may be overcome by employing a higher octane gasoline which resists knocking for powering the engine. This need for a higher octane gasoline as mileage accumulates has become known as the engine octane requirement increase (ORI) phenomenon. It is particularly advantageous if engine ORI can be substantially reduced or eliminated by preventing or modifying deposit formation in the combustion chambers of the engine.

Another problem common to internal combustion engines is the formation of intake valve deposits. Intake valve deposits interfere with valve closing and eventually will lead to valve burning. Such deposits interfere with valve motion and valve seating and tend to reduce the volumetric efficiency of the engine and to limit the maximum design power. Valve deposits may be produced from thermally and oxidatively unstable fuel or from lubricating oil oxidation products. The hard carbonaceous deposits produced collect in the tubes and runners that are part of the exhaust gas recirculation (EGR) flow. These deposits are believed to be formed from exhaust particles which are subjected to rapid cooling while mixing with the air-fuel mixture. Reduced EGR flow can result in engine knock and in nitric oxide, $NO_x$, emission increases. It would therefore be desirable to provide a motor fuel composition which minimizes or overcomes the formation of intake valve deposits.

2. Description of the Prior Art

Various motor fuel compositions and additives for minimizing or overcoming the formation of combustion chamber and intake valve deposits are described in the prior art.

For example, co-pending co-assigned application Ser. No. 07/896,700 filed Jun. 10, 1992 discloses a motor fuel additive composition of the formula:

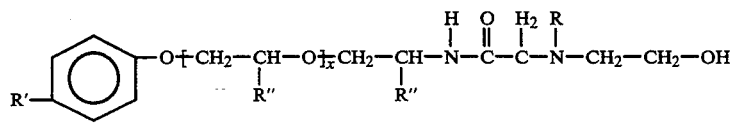

in which R represents a monovalent aliphatic radical having from 1 to 10 carbon atoms; R' represents a hydrocarbyl radical having from 4 to 30 carbon atoms; x has a value of from about 5 to 50; and R" represents a methyl radical or a mixture of hydrogen and methyl radicals.

Co-assigned U.S. Pat. No. 5,203,879, issued on Apr. 20, 1993, discloses a motor fuel additive composition of the formula:

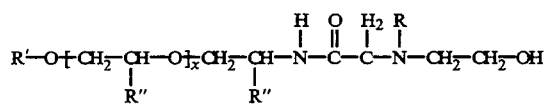

in which R represents a monovalent aliphatic radical having from 1 to 10 carbon atoms, R' represents an alkyl, an alicyclic or an alkyl-alicyclic radical having from 12 to 30 carbon atoms; x has a value of from about 5 to 50; and R" represents a methyl radical or a mixture of hydrogen and methyl radicals.

U.S. Pat. No. 4,747,851 discloses a novel polyoxyalkylene diamine compound of the formula:

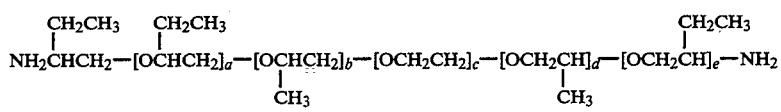

where c has a value from about 5-150, b+d has a value from about 5-150, and a+e has a value from about 2-12. Motor fuel compositions comprising the novel polyoxyalkylene diamine, alone or in combination with a polymer/copolymer additive are also disclosed.

U.S. Pat. No. 4,659,337 discloses the use of the reaction product of maleic anhydride, a polyether polyamide containing oxyethylene and oxypropylene ether moieties, and a hydrocarbyl polyamine in a gasoline motor fuel to reduce engine ORI and provide carburetor detergency.

The use of a mixture of (i) the reaction product of maleic anhydride, a polyether polyamine containing oxyethylene and oxypropylene ether moieties and a hydrocarbyl polyamine, and (ii) a polyolefin polymer/copolymer as an additive in motor fuel compositions to reduce engine ORI is described in U.S. Pat. No. 4,659,336.

U.S. Pat. No. 4,643,738 discloses a motor fuel composition comprising a deposit-control additive which is the reaction product of a dibasic acid anhydride, a polyoxyisopropylene diamine of the formula:

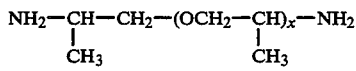

where x has a value of 2-50, and an N-alkyl-alkylene diamine.

U.S. Pat. No. 4,631,069 discloses an alcohol-containing motor fuel composition which additionally comprises an anti-wear additive which is the reaction product of a dibasic acid anhydride, a polyoxyisopropylene diamine of the formula:

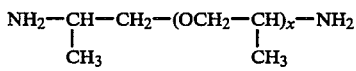

where x has a value of 2-68, and an N-alkyl-alkylene diamine.

U.S. Pat. No. 4,604,103 discloses a motor fuel deposit control additive for use in internal combustion engines which maintains cleanliness of the engine intake system without contributing to combustion chamber deposits or engine ORI. The additive disclosed is a hydrocarbyl polyoxyalkylene polyethylene amine of molecular weight range 300-2,500 having the formula:

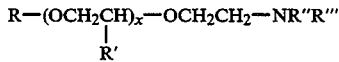

where R is a hydrocarbyl radical of from 1 to about 30 carbon atoms; R' is selected from methyl and ethyl; x is an integer from 5 to 30, and R" and R'" are independently selected from hydrogen and —(CH$_2$CH$_2$NH)$_y$—H, where y is an integer from 0 to 5.

U.S. Pat. No. 4,581,040 discloses the use of a reaction product as a deposit-inhibitor additive in fuel compositions. The reaction product is the condensation product of the process comprising (i) reacting a dibasic acid anhydride with a polyoxypropylene diamine of the formula:

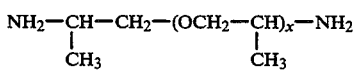

where x is a numeral of about 2-50, thereby forming a bis-maleamic acid; (ii) reacting said maleamic acid with a polyalkylene polyamine, thereby forming a condensate product; and (iii) recovering said condensate product.

U.S. Pat. No. 4,357,148 discloses a motor fuel additive useful in controlling ORI which is the combination of (a) an oil-soluble aliphatic polyamine containing at least one olefinic polymer chain, and (b) a polymer, copolymer, or corresponding hydrogenated polymer or copolymer of a C$_2$-C$_6$ mono-olefin with a molecular weight of 500-1,500.

U.S. Pat. No. 4,234,321 discloses a hydrocarbyl-poly(oxyalkylene) ureylene carbamate as a deposit control additive for fuels.

EP 297996 discloses an alkylphenylpoly(oxypropylene) aminocarbamate having a molecular weight ranging from 600 to 6000 for use in gasoline or diesel fuel compositions.

OBJECTS AND SUMMARY OF THE INVENTION

An object of this invention is to provide a novel additive reaction product which may be employed in fuel compositions and particularly in a motor fuel composition.

Another object is to provide a fuel additive reaction product and a motor fuel composition which inhibit the formation of intake valve deposits in an internal combustion engine.

Another object of this invention is to provide a fuel additive and a fuel composition which inhibit or reduce the formation of combustion chamber deposits in an internal combustion engine.

Yet another object of this invention is to provide a concentrate composition which may be added to a motor fuel to provide motor fuel compositions of the instant invention.

SUMMARY OF THE INVENTION

The intake valve and combustion chamber deposit-inhibiting additive of the invention is the reaction product prepared by reacting a 4-alkyl-2-morpholinone with hydrocarbyl oxypolyoxyalkylene amine.

The 4-alkyl-2-morpholinone reactant used to prepare the reaction product additive of the instant invention may be represented by the formula:

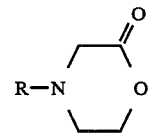

in which R represents a monovalent aliphatic radical having from 1 to 10 carbon atoms.

The hydrocarbyl oxypolyoxyalkylene amine reactant is represented by the formula:

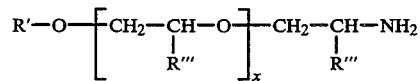

in which R' represents an alkyl, an alicyclic, or an alkyl-alicyclic radical having from 12 to 30 carbon atoms, or

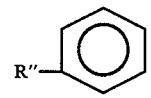

wherein R" represents a hydrocarbyl radical having from 4 to 30 carbon atoms, x has a value from about 5 to 50, R'" represents an ethyl radical or a mixture of methyl and ethyl radicals.

The final reaction product may be represented by the formula:

$$R'-O+CH_2-CH-O+_xCH_2-CH-N-C-CH_2-N-CH_2-CH_2-OH$$
$$\phantom{R'-O+CH_2-}\overset{|}{R'''}\phantom{-O+_x}\overset{|}{R'''}\phantom{-CH-}\overset{|}{H}\phantom{-C-}\overset{||}{O}\phantom{-CH_2-}\overset{|}{R'}$$

in which R, R', R", R''', and x have the values noted above.

The motor fuel composition of the invention comprises a mixture of hydrocarbons in the gasoline boiling range and a minor amount of the prescribed intake valve and combustion chamber deposit-inhibiting emulsion resistant additive of the invention.

DETAILED DESCRIPTION OF THE INVENTION

The intake valve and combustion chamber deposit-inhibiting additive of the invention is the reaction product of a 4-alkyl-2-morpholinone and the aminated propylene oxide and 1,2-butylene oxide adduct of a hydrocarbyl alcohol.

The 4-alkyl-2-morpholinone used to prepare the reaction product additive of the instant invention may be represented by the formula:

[morpholinone structure with R—N and O]

in which R represents a monovalent aliphatic radical having from 1 to 10 carbon atoms.

The hydrocarbyl oxypolyoxyalkylene amine reactant is represented by the formula:

$$R'-O-\left[CH_2-\underset{\underset{R'''}{|}}{CH}-O\right]_x-CH_2-\underset{\underset{R'''}{|}}{CH}-NH_2$$

in which R' represents an alkyl, an alicyclic or an alkyl alicyclic radical having from 12 to 30 carbon atoms or

[phenyl ring with R" substituent]

wherein R" represents a hydrocarbyl radical having from 4 to 30 carbon atoms, x has a value of from about 5 to 50, R''' is an ethyl radical or a mixture of methyl and ethyl radicals.

R' may be a straight chain, an isomeric branched chain, or a cyclo aliphatic hydrocarbyl radical including mixtures of these. Typical monovalent alkyl radicals include normal $C_{16}$–$C_{18}$ alkyl, $C_{12}$–$C_{20}$ alkyl, n-nonylcyclohexyl, n-oligomeric species with a chain length of $C_{20}$–$C_{30}$. Preferably, R' represents a saturated monovalent aliphatic radical having from about 12 to 24 carbon atoms, and more preferably an aliphatic radical having from about 14 to 20 carbon atoms.

R" may be a monovalent aliphatic radical having from about 6 to 24 carbon atoms, and more preferably an aliphatic radical having from about 8 to 20 carbon atoms. A particularly preferred value for R" is from 9 to 18 carbon atoms.

A preferred value for x is from about 6 to 30, with the most preferred value being from about 10 to 20.

As indicated above, the internal radical represented by the formula:

$$\left[CH_2-\underset{\underset{R'''}{|}}{CH}-O\right]_x$$

may be a mixture of propylene oxide and butylene oxide radicals. The ratio of propylene oxide radicals to butylene oxide radicals employed may range from about 0.01:9.99 to 9.99:0.01. A more preferred mole ratio range of propylene oxide to butylene oxide is from about 9:1 to 3:2.

The 4-alkyl-2-morpholinone reactant and the hydrocarbyl oxypolyoxyalkylene amine reactant are reacted in about a 1:1 mole ratio. While other mole ratios are contemplated, no significant advantage is realized in departing from about equimolar reaction ratios.

The additive reaction product of the invention may be represented by the formula:

$$R'-O+CH_2-\underset{\underset{R'''}{|}}{CH}-O+_xCH_2-\underset{\underset{R'''}{|}}{CH}-N-\overset{\overset{O}{||}}{C}-CH_2-\underset{\underset{H}{|}}{N}-CH_2-CH_2-OH$$

in which R, R', R", R''', and x have the values noted above.

Having described the invention in general terms, the following examples are offered as specific illustrations thereof. It is to be understood that these examples are illustrative only and that the invention is not limited thereby.

EXAMPLE I

A. Preparation of 10.5 Mole Propylene Oxide/3 Mole 1,2-Butylene Oxide Adduct of Nonylphenol Into a 10 gallon kettle were charged 12 pounds of nonylphenol and 302 grams of 45 percent aqueous potassium hydroxide. The reactor was then purged with prepurified nitrogen. Maintaining a nitrogen purge, the reactor was heated to 110° C. and the nonylphenol initiator dried to a water content of less than 0.1 percent using both vacuum and nitrogen stripping. A mixture of 33.2 lbs propylene oxide and 11.8 lb 1,2-butylene oxide was then reacted at 110°–115° C. at 60 psig over a six hour period. The reaction mixture was then digested at 115°–120° C. to an equilibrium pressure and purged with nitrogen for 30 minutes. The alkaline product was then neutralized at 95° C. by stirring for two hours with 951 grams Magnesol 30/40 adsorbent which was added in an aqueous slurry. Di-t-butyl p-cresol (7.7 grams) was then added to stabilize the product against oxidation. The neutralized product was then vacuum stripped to a minimum pressure at 110°–115° C., nitrogen stripped, and filtered. Properties of the finished product are given in Table I below.

TABLE I

| Properties | |
|---|---|
| Acid no., mg KOH/g | 0.009 |
| Hydroxyl no. mg KOH/G | 54.6 |
| Unsaturation, meq/g | 0.036 |

TABLE I-continued

| Properties | |
|---|---|
| Water, Wt. % | 0.04 |
| pH in 10:6 isopropanol-water | 8.1 |
| Color, Pt-Co | 4.0 |
| Sodium, ppm | 0.3 |
| Potassium, ppm | 2.0 |
| Viscosity, 77° F., CS | 323 |

B. Preparation of Hydrocarbyl oxypolyoxyalkylene Amine

To a tubular reactor filled with 1250 milliliters of a nickel catalyst was fed 1.35 lb/hr of the polyol (preparation A above), 1.35 lb/hr of ammonia, and 651/hr of hydrogen. The reactor was at 2000 psig and 215° C. The crude reactor effluent was charged to a clean dry kettle. It was then nitrogen stripped to 75° C. then placed under vacuum and heated to 100° C. The product had the following analysis:

| | meq/gram |
|---|---|
| Total acetylatables | 1.00 |
| Total amine | 0.964 |
| Primary amine | 0.961 |

C. Preparation of the Reaction Product of 4-Methyl-2-morpholinone and Nonylphenoxypolyoxyalkylene Amine To a 5-liter, three-necked flask equipped with a thermometer stirrer and nitrogen outlet, was charged 3089.6 g of hydrocarbyl oxypolyoxyalkylene amine (preparation B above) and 342.4 g of 4-methyl-2-morpholinone. The mixture was heated to 120° C. for three hours. The resulting product had the following analysis:

| Total Acetylatable | 0.87 meq/g |
|---|---|
| Total Amine | 0.855 meq/g | and may be represented by the formula:

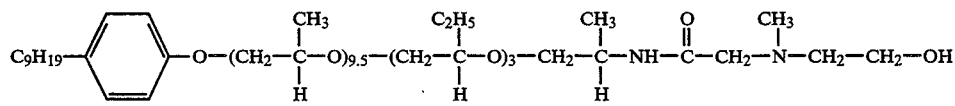

While shown as block copolymers, the propylene/butylene oxides can also be randomly distributed.

EXAMPLE II

A reaction product was prepared similar to Example I except that the polyol was prepared by reacting 10.5 moles of propylene oxide and 3.0 moles of 1,2-butylene oxide with a normal $C_{16}$-$C_{18}$ alkanol, which reaction product had the following formula:

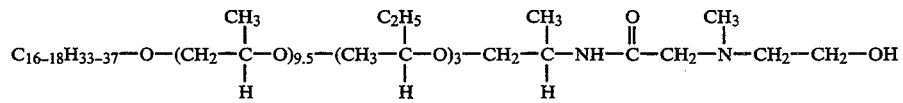

The additive of the invention was tested in motor fuels in comparison to commercial fuel compositions to demonstrate its effectiveness for reducing intake valve deposits and combustion chamber defaults.

Honda Generator Test

A test was developed to determine the intake valve detergency of an additive as well as to determine whether the additive will cause the intake valves to stick.

In small four-cylinder gasoline powered engines, the intake valves accumulate large amounts of deposits which interfere with the operation of the engine. A good detergent/dispersant is required to prevent the buildup of these deposits. The Honda Generator test was developed to measure the activity of additives in preventing the buildup of intake valve deposits (IVD) (keep clean). The measurements are done in two ways: (1) the intake valves at the end of the run are rated using the CRC method of rating (a valve with a rating of 10 is perfectly clean, and a valve rating of 6 or less denotes heavy deposit levels); and (2) intake valve deposit weights are obtained and also reported in grams.

Test Equipment

The Intake System Deposit/Intake Valve Stickiness Test consists of an electrical generator driven by a current technology gasoline engine, similar in many characteristics to modern vehicle engines. The generator set design allows the engine to be easily loaded by using the electrical generator as a dynamometer for the engine. The set operates at a governed speed of 3600 rpm and incorporates a twin cylinder, overhead camshaft, water-cooled engine described below in Table II.

TABLE II

| Engine Data for ES6500 Honda Generator | |
|---|---|
| Type: 4-stroke | Overhead cam, 2 cylinder |
| Cooling System: | Liquid cooled |
| Displacement: | 359 cc |
| Bore × Stroke: | 58 × 68 mm |
| Construction: | Aluminum head and block, fixed cast iron cylinder liners |
| Compression: | 8.5:1 |
| Maximum Power: | 9.1 Kw/3600 rpm |
| Maximum Torque: | 240 kg-cm |
| Fuel System: | Carburetor |
| Recommended Fuel: | Unleaded gasoline with min 86 (R + M)/2 octane |

The results of these tests are set forth in Table III below.

TABLE III

Honda Test Results

| | Example I | Commercial Additive PETROX |
|---|---|---|
| CRC Valve Rating | 9.99 | 6.03 |
| IVD Weight, grm. | 0.0006 | 0.269 |
| Stickiness | None | None |

The motor fuel containing the additive of the invention at 100 PTB gave excellent CRC valve ratings, virtually no deposits on the intake valves (4 mg or less), and exhibited no stickiness. The commercial additive package at 60 PTB showed a relatively poor CRC rating and had 269 mg IVD deposits. The commercial additive was free of valve stickiness. In this test, the additive of Example I in a motor fuel demonstrated excellent detergency and intake valve deposit keep clean properties.

Thermal Gravimetric Analysis (TGA)

TGA establishes the uniqueness of the hydrocarboxypolyoxyalkene morpholinones of the invention. Examination of TGA data in Table IV below indicates that Run 2 utilizing the additive of Example I is considerably more thermally labile than the products tested in Runs 1, and 3 to 5, inclusive. For example, at 200° C., 55.39% of Example I is decomposed, compared to 41.4–61.1% for Runs 1, 3 and 4, and only 34.5% for Run 5. Only 3.3% residue remains for Run 2 (Example I) at 295° C., indicating that it does not leave appreciable residue. Therefore, this polyether amine-morpholinone detergent should leave very clean intake valves and combustion chambers since it does not leave much deposits.

TABLE IV

| Run | | % Volatility Loss | |
|---|---|---|---|
| | | 200° C. | 295° C. |
| 1 | Competitive Additive | 41.4 | 95.5 |
| 2 | Example I | 55.3 | 96.7 |
| 3 | Commercial Additive | 61.1 | 95.1 |
| 4 | Commercial Additive | 54.3 | 89.2 |
| 5 | Commercial Additive oligomeric polyamine | 34.5 | 62.8 |

The above results demonstrate that the additive of the invention, Run 2, has an enhanced rate of decomposition as compared to commercial additives, and this property leads to surprisingly clean engine combustion chambers.

It is apparent to those of ordinary skill in the art that variations and departures from the exemplary matter described herein can be readily made within the scope of the specification and the appended claims.

What is claimed is:

1. An amido alkanolamine composition obtained by reacting, at a temperature of 10° C.–200° C.:
   (a) a 4-alkyl-2-morpholinone represented by the formula:

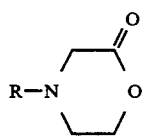

in which R represents a monovalent aliphatic radical having from 1 to 10 carbon atoms; and
   (b) a hydrocarbyl oxypolyoxyalkylene amine represented by the formula

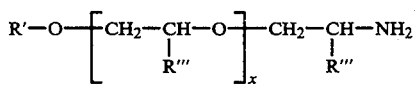

in which R' represents an alkyl, an alicyclic or an alkylalicyclic radical having from 12 to 30 carbon atoms or

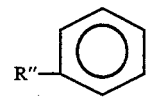

wherein R'' represents a hydrocarbyl radical having from 4 to 30 carbon atoms, x has a value of from about 5 to 50, and R''' is an ethyl radical or a mixture of methyl and ethyl radicals.

2. A composition according to claim 1 in which R represents a methyl radical.

3. A composition according to claim 1 in which R represents an isopropyl radical.

4. A composition according to claim 1 in which R' represents a monovalent aliphatic radical having from 6 to 30 carbon atoms.

5. A composition according to claim 1 in which R'' represents a monovalent aliphatic radical having from 6 to 24 carbon atoms.

6. A composition according to claim 5 in which said aliphatic radical has from 8 to 20 carbon atoms.

7. A composition according to claim 1 in which x has a value from about 10 to 20.

8. A composition according to claim 1 in which the alkylene oxide radical in said hydrocarbyl oxypolyoxyalkylene amine comprises a mixture of propylene oxide and butylene oxide in a mole ratio range from about 0.01:9.99 to about 9.99:0.01.

9. A composition according to claim 8 in which the mole ratio range of propylene oxide to butylene oxide is from about 9:1 to about 3:2.

10. A fuel composition containing from about 0.00015 to 1 weight percent of an amino reaction product prepared by reacting a 4-alkyl-2-morpholinone represented by the formula:

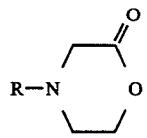

in which R represents a monovalent aliphatic radical having from 1 to 10 carbon atoms, with a hydrocarbyl oxypolyoxyalkylene amine reactant represented by the formula:

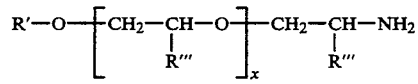

in which R' represents an alkyl, an alicyclic, or an alkylalicyclic radical having from 12 to 30 carbon atoms, or

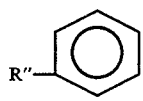

wherein R" represents a hydrocarbyl radical having from 4 to 30 carbon atoms, x has a value from about 5 to 50, and R'" represents an ethyl radical or a mixture of methyl and ethyl radicals.

11. A fuel composition according to claim 10 in which said fuel is a mixture of hydrocarbons in the gasoline boiling range.

12. A method for preparing an amido alkanolamine composition represented by the formula:

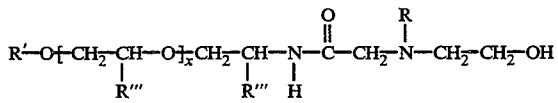

in which R' represents an alkyl, an alicyclic or an alkyl-alicyclic radical having from 12 to 30 carbon atoms or

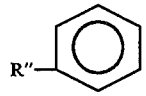

wherein R" represents a hydrocarbyl radical having from 4 to 30 carbon atoms, x has a value of from about 5 to 50, R'" is an ethyl radical or a mixture of methyl and ethyl radicals, which method comprises reacting a 4-alkyl-2-morpholinone represented by the formula:

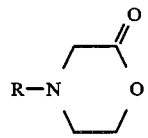

in which R represents a monovalent aliphatic radical having from 1 to 10 carbon atoms, with a hydrocarbyl oxypolyoxyalkylene amine reactant represented by the formula:

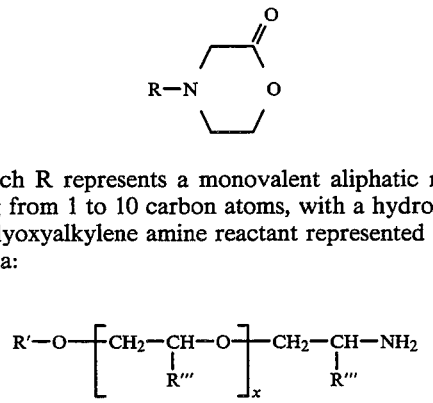

in which R, R', R" and R'" and x have the values noted above.

* * * * *